United States Patent [19]

Baldwin

[11] Patent Number: 5,108,004
[45] Date of Patent: Apr. 28, 1992

[54] ADDITIONAL STORAGE MEANS FOR A COVERED RECEPTACLE

[76] Inventor: Gene R. Baldwin, P.O. Box No. 1829, Rockford, Ill. 61110

[21] Appl. No.: 579,965

[22] Filed: Sep. 10, 1990

[51] Int. Cl.⁵ .......................................... B65D 85/00
[52] U.S. Cl. .................................. 220/522; 220/407; 220/23.86; 220/480; 206/554; 206/570
[58] Field of Search ............... 206/554, 570; 220/407, 220/521, 522, 480, 403, 23.86; 383/37

[56] References Cited

U.S. PATENT DOCUMENTS

| | | | |
|---|---|---|---|
| 908,663 | 1/1909 | Hamilton | 217/18 |
| 1,717,900 | 6/1929 | Swim | 206/554 |
| 2,736,454 | 2/1956 | McConnell | 220/522 |
| 3,044,233 | 7/1962 | Altman | 206/554 |
| 3,126,094 | 3/1964 | Arnold et al. | 206/554 |
| 3,361,294 | 1/1968 | Bjerum | 206/554 |
| 3,768,688 | 10/1973 | Linke | 220/522 |
| 4,207,983 | 6/1980 | Wolske | 206/554 |
| 4,280,643 | 7/1981 | Cordova et al. | 206/77.1 |
| 4,363,405 | 12/1982 | Cristie | 220/407 |
| 4,850,508 | 7/1989 | Lee | 220/407 |
| 4,928,830 | 5/1990 | Brewer | 206/570 |

FOREIGN PATENT DOCUMENTS

0624620  9/1978  U.S.S.R. .......................... 206/570

Primary Examiner—Stephen Marcus
Assistant Examiner—S. Castellano

[57] ABSTRACT

A storage bag adapted to be secured to the interior of a cover of a receptacle whereby the normally unused space therein can be utilized to store additional articles. A closed end of the bag is anchored in any suitable fashion to the interior of the cover with the opening in the bag being accessed to place articles therewithin.

11 Claims, 2 Drawing Sheets

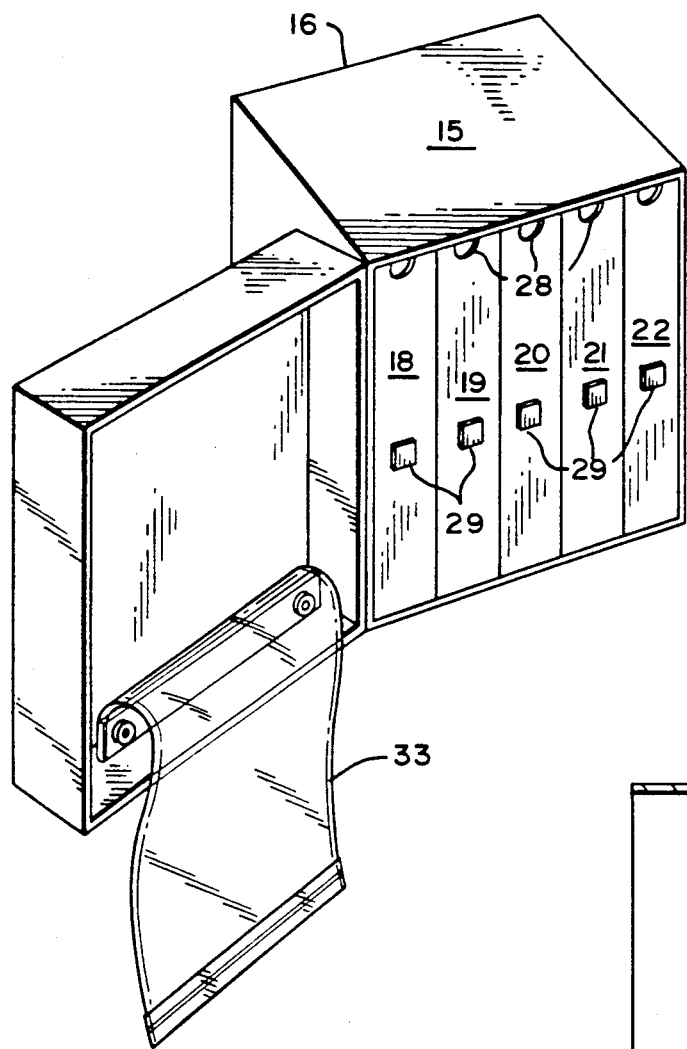
FIG. 4
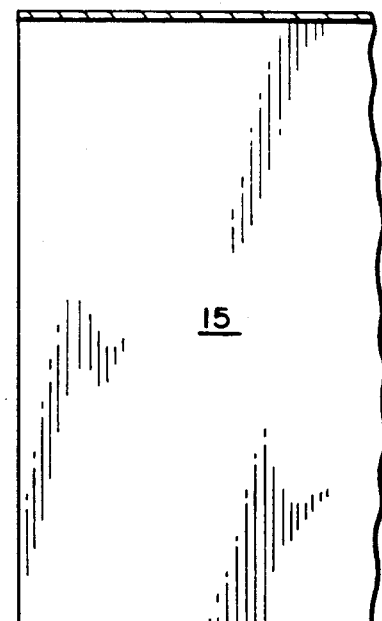
FIG. 5
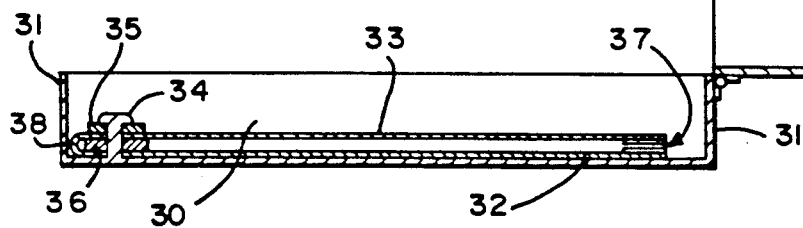

1

ADDITIONAL STORAGE MEANS FOR A COVERED RECEPTACLE

FIELD OF THE INVENTION AND RELATED ART

The present invention relates to readily increasing the storage area of a covered receptacle by utilizing the normally unused space within the cover.

A search in the U.S. Patent Office uncovered the following prior art.

U.S. Pat. No. 620,013
U.S. Pat. No. 2,788,822
U.S. Pat. No. 3,504,787
U.S. Pat. No. 4,207,983
U.S. Pat. No. 4,280,643

Of these, U.S. Pat. No. 620,013 is the most pertinent as it discloses a covered receptacle having a compartmented storage area as well as an area where bags can be mounted.

The remaining patents are pertinent for their showing of other receptacles for storing material therein and typify the prior art.

SUMMARY OF THE INVENTION

The present invention is directed to the utilization of the generally unused space in the cover of a conventional storage box for additional storage. This is accomplished by anchoring a bag or container within the confines of the cover which can be readily accessed for storing material therein. A somewhat conventional plastic bag is preferred for the storage purposes and in one embodiment is provided at its closed end with spaced openings which cooperate with spaced members anchored to the cover interior for anchoring the same therewith. It is contemplated that Velcro, magnets and adhesive could also be used.

BRIEF DESCRIPTION OF THE DRAWING

FIG. 4 shows a different orientation of the box and the bag oriented therein, and FIG. 5 is a cross-sectional view showing the bag 33 disposed within the cover.

DETAILED DESCRIPTION OF THE INVENTION

Figure 1:
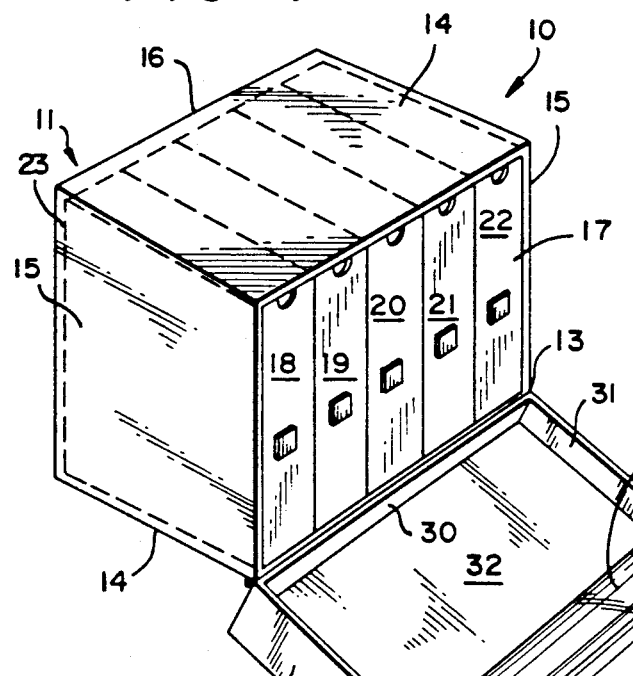
FIG. 1 is a perspective view of a storage box showing the cover in an open position with a storage bag anchored therein.
Figure 2:
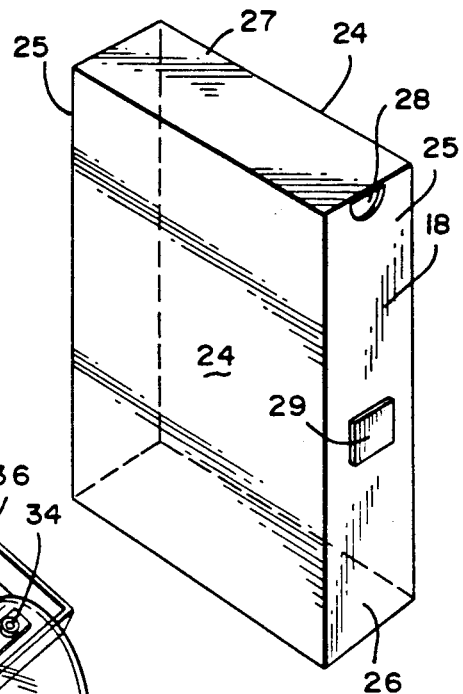
FIG. 2 is a detailed view of one of the containers that can be used within the storage box.

The organizer of the present invention is designated generally at 10 in FIG. 1 and is seen to be comprised of a box-like structure including a base 11 and a cover 12 hingedly or otherwise secured at 13 to the same. Base 11 is of rectangular configuration having side walls 14, 14, end walls 15, 15 and a bottom 16 thereby defining an open top 17. As seen in FIG. 1, the open top 17 permits access to the storage of a plurality of smaller boxes or containers 18, 19, 20, 21 and 22 therein, with it being understood that a fewer or larger number of the same can be provided as desired. The smaller boxes or containers 18-22 are of the same dimension and construction which permit a snug fit within the base 11 and can extend the depth thereof as shown in dotted outline 23 in FIG. 1. As seen in FIG. 2, each is comprises of upstanding sidewalls 24, 24, end walls 25, 25, a bottom wall 26, and top 27 with a thumb notch 28 of a pull tab 29 being utilized for grasping the same. These containers 18-22 can bed used to store like or unlike articles.

Figure 3:
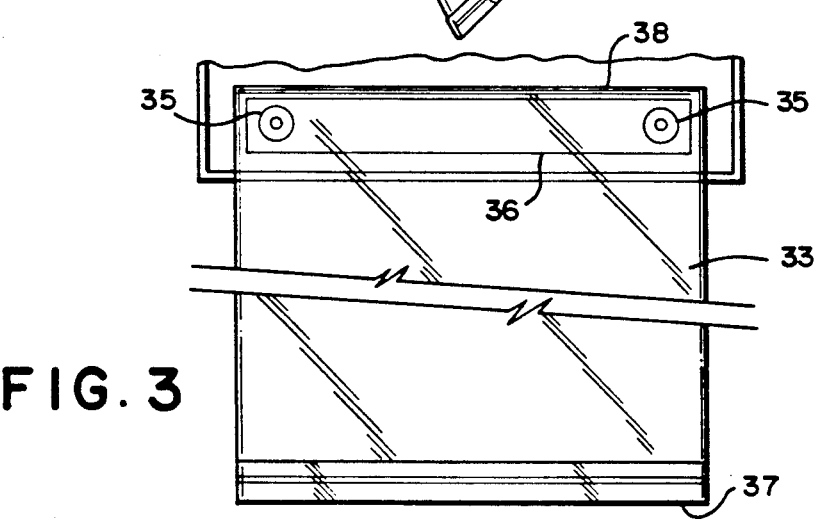
FIG. 3 is an assembly view showing the manner in which the bag is mounted to the interior of the storage box.

The cover 12 is opensided and is of the same length and width dimension as that of the base 11 for closely covering the same. The cover 12 in turn is formed by side walls 30, 30, end walls 31, 31 disposed about the periphery of the top 32 and defining a recessed cover 12. With continuing reference to FIG. 1 and as is more clearly seen in FIGS. 3 and 5, a bag 33 is removably secured to one side wall 30 of the cover, which is provided with a pair of spaced stakes, nails, pins or the like 34, 34 which cooperate with a pair of spaced grommets or washers 35, 35 formed in a reinforcing strip 36 secured to the closed end 38 of the bag 33. It is apparent then that the washers 35, 35 can than be placed over the stakes, pins, nails, etc., 34, 34 for maintaining the bag 33 in place within the cover 12. Once the bag 33 is removed from the interior of the cover 12, the end 37 is opened to place and remove articles while the closed end 38 remains anchored. The open end 37 can be maintained in a closed position by tie strings, wires embedded in and about the opening thereof, pins, or the like. The bag can be made from any material as desired which is dependent on the articles being stored and when the bag is accessed as seen in FIG. 4, i.e., when the base 11 and cover 12 have a vertical orientation, it has been found that if the bag is made a little wider than the dimensions of the cover it can be wedged or secured therein, maintaining it in place until needed. It is also considered to be within the scope of the present disclosure to have a plurality of bags rather than the single bag 33.

The primary use for the organizer of the present invention, although it is not limited thereto, is for the storage of first aid kits and the present design evolved in response to new OSHA regulations governing the provision and storage of complete and not partial first aid kits.

With reference to FIG. 1, the boxes 18-22, are individual first aid kits which when removed and opened for the necessary items therein such as scissors, gauze, iodine, etc., have remaining unused sterile items which can then be place din the bag 33 for storage purposes until such time that the same is needed. Box 18 is then replaced by another complete first aid box.

It is apparent that the organizer can be used for other purposes, such as filing documents in boxes 18-22 with non-wanted documents placed in the bag 33 until such time that the same can be discarded, shredded, etc.

Alternatively, it is considered to be within the purview of the disclosure to use strips of Velcro placed in the cover and on the bag for maintaining the bag therewith. Also, cooperating magnets and metal can be used for accomplishing the same purpose. As a further alternative, the anchoring strip 36 can be designed with ears to hold a roll for severable bags, whereby the topmost bag is utilized and thereafter removed when desired with a successive bag taking its place.

What is claimed is:

1. An organizer comprising a receptacle having a base, a cover defining an inner and outer surface, means movably connecting the cover to the base for closing and opening the same with respect to said base, a bag disposed within said cover, said bag having both a closed end portion and an open end portion, means removably securing only said closed end portion of said bag to said cover inner surface, said bag being of a length whereby the open end portion of the bag is removable from the inner surface of the cover while the closed end portion of the bag remains secured thereto, thereby allowing the open end portion of the bag to be suspended from the cover for accessing the same when the cover is in the open position.

2. The organizer of claim 1 wherein said means removably securing said closed end comprises a pair of spaced pin-like members disposed on said inner surface with said bag being provided with a pair of corresponding spaced openings at its closed end engaging said pin-like members.

3. The organizer of claim 2 wherein the closed end of the bag is provided with a reinforcing strip having the spaced openings formed therein.

4. The organizer of claim 3 wherein the open end of the bag is provided with openable closure means affording access to the interior thereof.

5. The organizer of claim 4 wherein the means removably connecting the cover to the base includes a hinge.

6. The organizer of claim 5 wherein the cover is of the same general dimension as said base for securing at least one container within the base when the cover is closed.

7. The organizer of claim 6 wherein a plurality of smaller containers are disposed in said base.

8. The organizer of claim 1 wherein said means removably securing said closed end is Velcro disposed both on said inner surface and said bag respectively.

9. The organizer of claim 1, wherein magnets and magnetic material are disposed on the bag and cover to hold the bag therein.

10. An organizer comprising a receptacle having a base, a cover defining an inner and outer surface, means movably connecting the cover to the base for closing and opening the same with respect to said base, a bag having both a closed end and an open end disposed within said cover, means removably securing said closed end to said inner surface and comprising a pair of spaced pin-like members disposed on said inner surface with said bag being provided with a pair of corresponding spaced openings at its closed end engaging said pin-like members with said bag having a dimension greater than that of said cover to permit the same to be frictionally held therewithin and said bag being of a length whereby the open end is capable of being removed from the inner surface of the cover and allowed to be suspended therefrom for accessing the same.

11. An organizer comprising a receptacle having a base, a cover defining an inner and outer surface, means movably connecting the cover to the base for closing and opening the same with respect to said base, a bag having both a closed end and an open end disposed within said cover, means removably securing said closed end to said inner surface and comprising a support rod disposed on said inner surface and a roll of severable bags disposed thereon with the bags being of a greater dimension than that of the cover to permit the lead-most one of be frictionally held therewithin.

* * * * *